US006342200B1

(12) United States Patent
Rouleau et al.

(10) Patent No.: US 6,342,200 B1
(45) Date of Patent: Jan. 29, 2002

(54) PROCESS FOR PREPARING A ZEOLITE WITH STRUCTURE TYPE EUO

(75) Inventors: Loic Rouleau, Oullins; Sylvie Lacombe, Rueil-Malmaison; Fabio Alario, Neuilly sur Seine; Elisabeth Merlen, Rueil-Malmaison; Frédéric Kolenda, Francheville le Haut; Julia Magne-Drisch, Vilette de Vienne, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/432,120

(22) Filed: Nov. 2, 1999

(30) Foreign Application Priority Data

Nov. 2, 1998 (FR) .............................. 98/13839
Dec. 23, 1998 (FR) .............................. 98/16412

(51) Int. Cl.⁷ ................................ C01B 39/04
(52) U.S. Cl. ...................... 423/709; 423/708
(58) Field of Search ................ 423/708, 709; 502/66, 73, 74

(56) References Cited

U.S. PATENT DOCUMENTS

| 3,733,390 A | * | 5/1973 | Robson ..................... 423/709 |
| 3,808,326 A | * | 4/1974 | McDaniel et al. .......... 423/709 |
| 4,275,047 A | | 6/1981 | Whittam |
| 4,503,024 A | * | 3/1985 | Bourgogne et al. ......... 423/709 |
| 4,537,754 A | | 8/1985 | Casci et al. |
| 4,640,829 A | | 2/1987 | Rubin |
| 4,650,655 A | | 3/1987 | Chu et al. |
| 4,695,667 A | | 9/1987 | Sumitani et al. |
| 4,818,509 A | * | 4/1989 | Dwyer et al. ............... 423/709 |

FOREIGN PATENT DOCUMENTS

| EP | 0 042 226 | 12/1981 |
| EP | 0 051 318 | 5/1982 |
| EP | 0 127 399 | 12/1984 |
| EP | 0 338 897 | 10/1989 |

OTHER PUBLICATIONS

The Synthesis and Characterisation of Zeolite EU–1, J. L. Casci et al., Proceedings of the Sixth International Zeolite Conference, Butterworth & Co., Guidford, UK, 1984, pp. 894–904.

\* cited by examiner

*Primary Examiner*—David R. Sample
(74) *Attorney, Agent, or Firm*—Millen, White, Zelano & Branigan, P.C.

(57) ABSTRACT

The present invention concerns a process for preparing a zeolite with structure type EUO comprising at least one element X selected from silicon and germanium and at least one element T selected from iron, aluminium, gallium, boron, titanium, vanadium, zirconium, molybdenum, arsenic, antimony, chromium and manganese, characterized in that seeds of at least one zeolitic material are used comprising at least one element X' selected from silicon and germanium and at least one element T' selected from iron, aluminium, gallium, boron, titanium, vanadium, zirconium, molybdenum, arsenic, antimony, chromium and manganese with a ratio X'/T' of less than 200, said seeds being different from the zeolite with structure type EUO being prepared. The present invention also concerns the use of the zeolite obtained as a catalyst in a process for converting hydrocarbon-containing feeds, as an adsorbent to control pollution and as a molecular sieve for separation, and more particularly as a catalyst in a process for isomerizing aromatic compounds containing 8 carbon atoms.

13 Claims, No Drawings

PROCESS FOR PREPARING A ZEOLITE WITH STRUCTURE TYPE EUO

CROSS-REFERENCE TO RELATED APPLICATION

This application is related to applicants concurrently filed application Ser. No. 09/432,122, entitled "Process For Preparing A Zeolite With Structure Type EUO Using Structuring Agent Precursors And Its Use As An AC8 Isomerisation", based on French Applications 98/13.773 filed Nov. 2, 1998 and 98/16.411 filed Dec. 23, 1998.

TECHNICAL FIELD

The present invention relates to a novel process for preparing zeolites with structure type EUO. Zeolites with structure type EUO synthesised using the process of the present invention include EU-1, TPZ-3 zeolite and ZSM-50 zeolite and generally have the following formula in the anhydrous form: 0 to 20 $R_2O$: 0–10 $T_2O_3$: 100$XO_2$ where R represents a monovalent cation or 1/n of a valency cation n, X represents silicon and/or germanium, T represents at least one element selected from aluminium, iron, gallium, boron, titanium, vanadium, zirconium, molybdenum, arsenic, antimony, chromium and manganese.

Zeolites with structure type EUO are generally synthesised by mixing, in an aqueous medium, at least one source of silica and/or germanium and at least one source of at least one element selected from aluminium, iron, gallium, boron, titanium, vanadium, zirconium, molybdenum, arsenic, antimony, chromium and manganese in the presence of an organic nitrogen-containing compound acting as a structuring agent, or corresponding degradation products or precursors. The mixture is generally maintained at a certain temperature until the zeolite crystallises.

The present invention also relates to a process for preparing a catalyst based on a zeolite with structure type EUO, said zeolite being obtained using a novel synthesis mode. The invention also relates to a process for isomerising aromatic compounds containing 8 carbon atoms also known as "aromatic C8 cuts" in the presence of this catalyst based on a zeolite with structure type EUO.

Isomerising ethylbenzene to xylenes requires the presence of a group VIII metal. Optimised formulations based on mordenite and a group VIII metal result in catalysts for which side reactions remain non negligible. Examples which can be cited are naphthene ring opening reactions followed or otherwise by cracking or dismutation and transalkylation of C8 aromatic compounds, which lead to the formation of undesirable aromatic compounds. The discovery of new, more selective catalysts is thus of particular importance.

PRIOR ART

The EU-1 zeolite with structure type EUO, which has already been described in the prior art, has a unidimensional microporous framework, with a pore diameter of 4.1×5.7 Å (1 Å=1 Angstrom=$10^{-10}$ m) ("Atlas of Zeolite Structure Types", W. M. Meier and D. H. Olson, $4^{th}$ edition, 1996). Further, N. A. Briscoe et al. stated in their article in the review Zeolites (1988, 8, 74) that 6.8×5.8 Å. A method for synthesising EU-1 zeolite and its physico-chemical characteristics have been described in European patent EP-A-0 042 226. The synthesis mode comprises mixing a silicon and/or germanium oxide and an oxide of at least one element selected from aluminium, iron, gallium and boron in the presence of a structuring agent comprising at least one alkylated polymethylene α-ω diammonium derivative, a degradation product of that derivative or precursors of that derivative.

The synthesis of EU-1 zeolite from silicalite or EU-1 seeds has been described in the literature (Casci, J. L.; Whittam, T. V.; Lowe B. M., Proc. Int. Zeolite Conf., $6^{th}$ (1984), Meeting Date 1983, 984–904, Editors Olson, David, Bisio, Allilio; publisher: Butterworth, Guildford (UK).

U.S. Pat. No. 4,640,829 concerns a ZSM-50 zeolite which according to the "Atlas of Zeolite Structure Types", W. M. Meier and D. H. Olson, $4^{th}$ Edition, 1996, has structure type EUO. That patent describes a mode of synthesising ZSM-50 comprising mixing a source of alkali metal ions, dibenzyldimethylammonium ions or precursors thereof, silicon oxide, aluminium oxide and water.

EP-A-0 051 318 relates to TPZ-3 zeolite which, according to the "Atlas of Zeolite Structure Types", W. M Meier and D. H. Olson, $4^{th}$ edition, 1996, has the same EUO structure type as EU-1 zeolite. Preparation of the zeolite comprises mixing a soluble alkali metal compound, a 1,6-N,N,N,N', N',N'-hexamethylhexamethylenediammonium compound, a compound which can provide silicon and a compound which can provide alumina, at a temperature of more than 80° C.

SUMMARY OF THE INVENTION

The present invention concerns a process for preparing a zeolite with structure type EUO comprising at least one element X selected from silicon and germanium and at least one element T selected from iron, aluminium, gallium, boron, titanium, vanadium, zirconium, molybdenum, arsenic, antimony, chromium and manganese, characterized in that seeds of at least one zeolitic material comprising at least one element X' selected from silica and germanium and at least one element T' selected from iron, aluminium, gallium, boron, titanium, vanadium, zirconium, molybdenum, arsenic, antimony, chromium and manganese is used, said seeds being different from the zeolite with structure type EUO which is prepared. The zeolite seeds used have an X'/T' ratio of less than 200. The present invention also concerns the use of the EUO zeolite as a catalyst, said catalyst also comprising at least one element from group VIII of the periodic table and which can be used in a process for isomerising aromatic compounds containing 8 carbon atoms per molecule.

IMPORTANCE OF THE INVENTION

The process of the invention can reduce the crystallisation time of the EUO zeolite after forming the mixture, to achieve a maximum yield of pure product, which reduces the costs. The reaction medium composition can have a wider range, which increases flexibility.

Thus, the Applicant has discovered that synthesis of a zeolite with structure type EUO characterized by using seeds of at least one zeolitic material different from the material to be synthesised can achieve the advantages cited above, i.e., an advantage as regards time, pure product yield and flexibility in reaction mixture composition.

DESCRIPTION OF THE INVENTION

The invention concerns a process for preparing a zeolitic material with structure type EUO comprising at least one element X selected from silicon and germanium and at least one element T selected from iron, aluminium, gallium, boron, titanium, vanadium, zirconium, molybdenum, arsenic, antimony, chromium and manganese, characterized in that seeds of at least one zeolitic material comprising at least one element X' selected from silica and germanium and at least one element T' selected from iron, aluminium, gallium, boron, titanium, vanadium, zirconium, molybdenum, arsenic, antimony, chromium and manganese is used, said seeds being different from the zeolite with structure type EUO which is prepared. The zeolite seeds used have an X'/T' ratio of less than 200.

The different between the zeolite with structure type EUO which is to be synthesised and the zeolitic material introduced as seeds lies either in the difference in structure type, or in the difference in chemical composition of the crystalline framework, or in the difference in structure type and the difference in chemical composition of the crystalline framework.

The preparation process of the invention comprises mixing, in an aqueous medium, at least one source of at least one element X selected from silicon and germanium, at least one source of at least one element T selected from aluminium, iron, gallium, boron, titanium, vanadium, zirconium, molybdenum, arsenic, antimony, chromium and manganese, at least one nitrogen-containing organic compound Q selected from alkylated polymethylene α-ω diammonium derivatives, dibenzyldimethylammonium salts, an amine degradation product corresponding to said organic compound Q, or corresponding precursors of said organic compound Q, and seeds S of a zeolitic material. The invention is characterized in that the seeds used comprise at least one zeolitic material different from the EUO zeolite which is to be prepared. The mixture reaction is maintained until the zeolite crystallises.

The alkylated polymethylene α-ω diammonium derivative acting as a structuring agent, used more particularly for the synthesis of EU-1 zeolite or TPZ-3 zeolite, is defined by the formula: $R_1R_2R_3N^+(CH_2)_nN^+ R_4R_5R_6$, n being in the range 3 to 12 and $R_1$ to $R_6$, which may be identical or different, representing alkyl or hydroxyalkyl radicals containing 1 to 8 carbon atoms; up to five $R_1$ to $R_6$ radicals can be hydrogen.

Thus seeds of at least one solid with structure type LTA such as A zeolite, with structure type LTL, structure type FAU such as X and Y zeolites, structure type MOR, structure type MAZ, structure type OFF, structure type FER, structure type ERI, structure type BEA, structure type MFI such as ZSM-5 and silicalite, structure type MTW, structure type MTT, structure type LEV, structure type TON, structure type NES such as NU-87 zeolite, or a NU-85, NU-86, NU-88 or IM-5 zeolite or a zeolite with structure type EUO with a chemical composition of the crystalline framework which is different from the chemical composition of the crystalline framework of the EUO zeolite to be prepared, in particular with different X'/T' ratios, these being less than 200. Preferably, the seeds for synthesising a zeolite with structure type EUO are constituted by seeds of zeolites with structure type LTA, FAU, MOR, MFI, EUO with an X'/T' ratio of less than 200.

The zeolitic materials acting as seeds can be introduced at any point in the preparation of the zeolite which is to be synthesised. The seeds can be introduced at the same time as the sources of the elements X and T, or as organic structuring agent Q, or the seeds can be introduced first into the aqueous mixture, or the seeds can be introduced after introducing the sources of elements X and T and the structuring agent. Preferably, the seeds are introduced after at least partial homogenisation of the aqueous mixture containing sources of elements X and T and the structuring agent.

The zeolitic materials acting as seeds can be introduced during synthesis of the zeolite which is to be synthesised in a number of forms. The seeds can be introduced after having undergone at least one of the steps selected from the following steps: washing, drying, calcining and ion exchange. The seeds can also be introduced in the as synthesised form.

The seed particle size can have an influence on the synthesis process and must preferably have the desired size. The term "zeolite seed particle" means a either a zeolite crystal or an aggregate of zeolite crystals. Thus the size of at least the major portion of the seed particles introduced during preparation of the zeolitic material is in the range 0.001 to 500 μm, preferably in the range 0.005 to 250 μm.

In one particular implementation, independent or otherwise of the preceding implementation, it may be advantageous to add at least one alkali metal or ammonium salt P to the reaction medium. Examples which can be cited are strong acid radicals such as bromide, chloride, iodide, sulphate, phosphate or nitrate, or weak acid radicals such as organic acid radicals, for example citrate or acetate. This salt can accelerate crystallisation of EUO zeolites from the reaction mixture.

In the process of the invention, the reaction mixture generally has the following composition, expressed in the oxide form:

| | |
|---|---|
| $XO_2/T_2O_3$ (mol/mol) | at least 10 |
| $OH^-/XO_2$ (mol/mol) | 0.002 to 2.0 |
| $Q/XO_2$ (mol/mol) | 0.002 to 2.0 |
| $Q/(M^+ + Q)$ (mol/mol) | 0.1 to 1.0 |
| $H_2O/XO_2$ (mol/mol) | 1 to 500 |
| $P/XO_2$ (mol/mol) | 0 to 5 |
| $S/XO_2$ (g/g) | 0.0001 to 0.1 |

Preferably, the reaction mixture has the following composition, expressed in the oxide form:

| | |
|---|---|
| $XO_2/T_2O_3$ (mol/mol) | at least 12 |
| $OH^-/XO_2$ (mol/mol) | 0.005 to 1.5 |
| $Q/XO_2$ (mol/mol) | 0.005 to 1.5 |
| $Q/(M^+ + Q)$ (mol/mol) | 0.1 to 1.0 |

-continued

|  |  |
|---|---|
| $H_2O/XO_2$ (mol/mol) | 3 to 250 |
| $P/XO_2$ (mol/mol) | 0 to 1 |
| $S/XO_2$ (g/g) | 0.0005 to 0.07 | and still more preferably, the reaction mixture has the following composition, expressed in the oxide form:

|  |  |
|---|---|
| $XO_2/T_2O_3$ (mol/mol) | at least 15 |
| $OH^-/XO_2$ (mol/mol) | 0.01 to 1 |
| $Q/XO_2$ (mol/mol) | 0.01 to 1 |
| $Q/(M^+ + Q)$ (mol/mol) | 0.1 to 1.0 |
| $H_2O/XO_2$ (mol/mol) | 5 to 100 |
| $P/XO_2$ (mol/mol) | 0 to 0.25 |
| $S/XO_2$ (g/g) | 0.001 to 0.04 | where

X is silicon and/or germanium,

T is at least one element selected from aluminium, iron, gallium, boron, titanium, vanadium, zirconium, molybdenum, arsenic, antimony, chromium and manganese;

$M^+$ represents an alkali metal or an ammonium ion;

Q represents the organic structuring agent or the decomposition products corresponding to said derivative or precursors of said derivative;

S represents zeolite seeds expressed in their as synthesised, dried, calcined or exchanged form with an X'/T' ratio of less than 200;

P represents the alkali metal or ammonium salt.

M and/or Q can be present in the form of hydroxides or salts of inorganic or organic acids provided that the $OH^-/XO_2$ criterion is satisfied.

The quantity of seeds introduced with respect to the quantity of oxide $XO_2$ is in the range 0.001% to 10%, preferably in the range 0.05% to 7%, more preferably in the range 0.1% to 4%.

The synthesis of the EUO zeolite using the process of the present invention is carried out using an organic compound Q acting as a structuring agent.

When synthesising EU-1 zeolite, the preferred starting alkylated polymethylene α-ω diammonium derivatives Q are, inter alia, alkylated hexamethylene α-ω-diammonium derivatives and especially methylated hexamethylene α-ω diammonium derivatives, more preferably still 1,6-N,N,N,N',N',N'-hexamethylhexamethylene α-ω diammonium salts, for example the halide, hydroxide, sulphate, silicate or aluminate.

The alkylated polymethylene α-ω diammonium derivatives can be obtained from precursors. Suitable precursors of the starting alkylated polymethylene α-ω diammonium derivatives are in particular the related diamines together with alcohols, alkyl halides, alkanediols or the related alkane dihalides together with alkylamines. They can be mixed as they are with the other reactants or they can be preheated together in the reaction vessel, preferably in solution before adding the other reactants necessary for synthesis of the EU-1 zeolite.

When preparing the ZSM-50 zeolite, the organic structuring agent Q can be a dibenzyldimethylammonium salt such as the halide, hydroxide, sulphate, silicate or aluminate.

Dibenzyldimethylammonium salts can be obtained from precursors. Suitable precursors are benzyldimethylamine and a benzyl halide or benzyl alcohol. They can be used as they are in situ or they can be preheated together in the reaction vessel, preferably in solution, before adding the other reactants necessary for synthesis of the ZSM-50 zeolite.

The preferred alkali metal ($M^+$) is sodium. The preferred element X is silicon. The preferred element T is aluminium.

The silicon source can be any one in normal used envisaged for zeolite synthesis, for example solid powdered silica, silicic acid, colloidal silica or dissolved silica. Powdered silicas which can be used include precipitated silicas, in particular those obtained by precipitation from a solution of an alkali metal silicate such as "Zeosil" or "Tixosil" produced by Rhône-Poulenc, fumed silicas such as "Aerosil" produced by Degussa and "Cabosil" produced by Cabot, and silica gels. Colloidal silicas with a variety of granulometries can be used, such as those sold under trade marks "LUDOX" from Dupont, and "SYTON" from Monsanto.

Particular dissolved silicas which can be used are commercially available soluble glasses or silicates containing: 0.5 to 6.0 and in particular 2.0 to 4.0 moles of $SiO_2$ per mole of alkali metal oxide and silicates obtained by dissolving silica in an alkali metal hydroxide, a quaternary ammonium hydroxide or a mixture thereof.

More advantageously, the aluminium source is sodium aluminate, but it can also be aluminium, an aluminium salt, for example a chloride, nitrate or sulphate, an aluminium alcoholate or alumina itself which should preferably be in a hydrated or hydratable form, such as colloidal alumina, pseudoboehmite, boehmite, gamma alumina or a trihydrate.

Mixtures of the sources cited above can be used. Combined sources of silicon and aluminium can also be used, such as amorphous silica-aluminas or certain clays.

The reaction mixture is normally caused to react under autogenous pressure, optionally adding a gas, for example nitrogen, at a temperature in the range 85° C. to 250° C. until zeolite crystals form, which can take from 1 minute to several months depending on the reactant composition, the mode of heating and the mixture, the working temperature and the degree of stirring. Stirring is optional but preferable, as it reduces the reaction time.

When the reaction is over, the solid phase is collected on a filter and washed and is then ready for subsequent operations such as drying, calcining and ion exchange.

To obtain the hydrogen form of the EUO zeolite, ion exchange can be carried out using an acid, in particular a strong mineral acid such as hydrochloric, sulphuric or nitric acid, or with an ammonium compound such as ammonium chloride, sulphate or nitrate. Ion exchange can be carried out by diluting once or more with the ion exchange solution. The EUO zeolite can be calcined before or after ion exchange or between two ion exchange steps, preferably before ion exchange to eliminate all absorbed organic substances, provided that ion exchange is thereby facilitated.

As a general rule, the cation or cations of the zeolite with structure type EUO can be replaced by one or more cations of any metal, in particular those from groups IA, IB, IIA, IIB, IIIA and IIIB (including the rare earths), VIII (including the noble metals), also lead, tin and bismuth (the periodic table is that shown in the "Handbook of Physics and Chemistry", 76$^{th}$ edition). Exchange is carried out using any water-soluble salt containing the appropriate cation.

The present invention also concerns the use of the zeolite prepared using the process of the present invention as an adsorbent to control pollution, as a molecular sieve for separation and as an acidic solid for catalysis in the fields of refining and petrochemistry.

As an example, when it is used as a catalyst, the EUO zeolite can be associated with an inorganic matrix which can be inert or catalytically active, and with an active phase. The inorganic matrix can be present simply as a binder to keep the small particles of zeolite together in the different known forms of catalysts (extrudates, beads, powders), or it can be added as a diluent to impose a degree of conversion on a process which would otherwise proceed at too high a rate leading to clogging of the catalyst as a result of increased coke formation. Typical inorganic diluents are support materials for catalysts such as silica, the different forms of alumina and kaolinic clays, bentonites, montmorillonites, sepiolite, attapulgite, fuller's earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$ or any combination of these compounds.

The zeolite with structure type EUO can also be associated with at least one other zeolite and acts as the principal active phase or as an additive.

The inorganic matrix can be a mixture of different compounds, in particular an inert phase and an inorganic phase.

The metallic phase in introduced into the zeolite alone, the inorganic matrix alone or into the inorganic matrix-zeolite ensemble, by ion exchange or impregnation with cations or oxides selected from the following: Cu, Ag, Ga, Mg, Ca, Sr, Zn, Cd, B, Al, Sn, Pb, V, P, Sb, Cr, Mo, W, Mn, Re, Fe, Co, Ni, Pt, Pd, Ru, Rh, Os, Ir and any other element from the periodic table.

Catalytic compositions comprising the zeolite with structure type EUO can be applied to isomerisation, transalkylation and dismutation, alkylation and dealkylation, hydration and dehydration, oligomerisation and polymerisation, cyclisation, aromatisation, cracking and hydrocracking, reforming, hydrogenation and dehydrogenation, oxidation, halogenation, amine synthesis, hydrodesulphurisation and hydrodenitrogenation, catalytic elimination of oxides of nitrogen, ether formation and hydrocarbon conversion and to the synthesis of organic compounds in general, these reactions involving saturated and unsaturated aliphatic hydrocarbons, aromatic hydrocarbons, oxygen-containing organic compounds and organic compounds containing nitrogen and/or sulphur, also organic compounds containing other functional groups.

In particular, the present invention also concerns the use of the EUO zeolite in a catalyst for isomerising aromatic compounds containing 8 carbon atoms, said catalyst also comprising at least one element from group VIII of the periodic table and at least one binder.

The catalyst of the present invention, formed into beads or extrudates, thus contains:

at least one zeolite with an EUO structure, for example EU-1 zeolite, synthesised in the presence of seeds using the method described above;

at least one metal from group VIII of the periodic table, preferably selected from the group constituted by palladium and platinum and still more preferably platinum;

at least one binder, preferably alumina;

optionally, at least one metal from the group formed by elements from groups IB, IIB, IIIA, IVA, VIB and VIIIB of the periodic table, preferably tin or indium;

optionally, sulphur;

said catalyst being characterized in that it is prepared using a novel method for synthesising the zeolite with structure type EUO comprised in the catalyst, which method can reduce the synthesis time with a maximum yield of pure product, which reduces manufacturing costs.

More precisely, the catalyst prepared using the process of the present invention generally comprises, with respect to the catalyst weight:

1% to 90%, preferably 3% to 60% and more preferably 4% to 40% by weight of at least one zeolite with structure type EUO, obtained using the novel synthesis mode, comprising at least one element X selected from germanium and silicon and at least one element T selected from the group formed by aluminium, iron, gallium, boron, titanium, vanadium, zirconium, molybdenum, arsenic, antimony, chromium and manganese, preferably aluminium and boron, with an atomic ratio X/T being 5 or more. Said zeolite is at least partially in the acidic form, i.e., in the hydrogen ($H^+$) form, the sodium content being such that the Na/T atomic ratio was less than 0.5, preferably less than 0.1, more preferably less than 0.02;

0.01% to 2% and preferably 0.05% to 1.0% by weight of at least one metal from group VIII of the periodic table, preferably selected from the group formed by platinum and palladium and more preferably platinum;

optionally, 0.01% to 2%, preferably 0.05% to 1.0% by weight, of at least one metal from the group formed by groups IB, IIB, IIIA, IVA, VIB and VIIB of the periodic table, preferably selected from the group formed by tin and indium;

optionally, sulphur the quantity of which is such that the ratio of the number of sulphur atoms to the number of deposited group VIII metal atoms is in the range 0.5 to 2, limits included;

the complement to 100% by weight of at least one binder, preferably alumina.

Any zeolite with structure type EUO which is known to the skilled person and obtained using the synthesis mode described in the present patent is suitable for the catalyst used in the present invention. Thus, for example, the zeolite used as a base to prepare said catalyst can be as synthesised EU-1 zeolite having the required specificities regarding the X/T ratio. Generally, calcining can then be carried out, then at least one ion exchange in at least one $NH_4NO_3$ solution so as to obtain a zeolite with a greater or lesser residual sodium content.

The binder (or matrix) in the catalyst prepared using the process of the present invention generally consists of at least one element selected from the group formed by clays, magnesia, aluminas, silicas, titanium oxide, boron oxide, zirconia, aluminium phosphates, titanium phosphates, zirconium phosphates and silica aluminas. Charcoal can also be used. Preferably, the binder is alumina.

The zeolite with structure type EUO, for example EU-1 zeolite, in the catalyst of the invention, is at least partially, preferably practically completely in its acid form, i.e., in the hydrogen form ($H^+$), the sodium content preferably being such that the Na/T atomic ratio is less than 0.5, preferably less than 0.1, more preferably less than 0.02.

The metals can be introduced either all in the same way or using different techniques, at any time in the preparation, before or after forming and in any order. Further, intermediate treatments such as calcining and/or reduction can be carried out between depositions of the different metals.

The preparation of the matrix, introduction of the metals and forming of the catalyst can be carried out using any method known to the skilled person. Thus at least one group VIII element is introduced into the zeolite or onto the binder, preferably onto the binder before or after forming.

One preferred method consists of producing a mixture of the matrix and the zeolite followed by forming. Forming is generally followed by calcining, generally at a temperature in the range 250° C. to 600° C. At least one element from group VIII of the periodic table is introduced after this calcining, preferably by selective deposition onto the binder. Said elements are in practice deposited in an amount of more than 90% in total on the binder and in a manner which is known to the skilled person by controlling the parameters used during said deposition, such as the nature of the precursor used to carry out said deposition. Optionally, at least one element from the group formed by elements from groups IB, IIB, IIIA, IVA, VIB and VIIB are added. Elements from group VIII and groups IB, IIB, IIIA, IVA, VIB and VIIB are added either separately at any stage of the catalyst preparation, or simultaneously in at least one unitary step. When an element from at least one of groups IB, IIB, IIIA, IVA, VIB and VIIB is separately added, then preferably it is added prior to adding the group VIII element.

At least one group VIII element is deposited, preferably onto the zeolite-binder mixture which has already been formed by any process known to the skilled person. Such deposition is, for example, carried out using a dry impregnation step, excess impregnation or ion exchange. Any precursor can be used to deposit these elements. As an example, and preferably, anionic exchange is carried out with hexachloroplatinic acid and/or hexachloropalladic acid in the presence of a competing agent, for example hydrochloric acid. With such precursors, the metal is in practice deposited in an amount of more than 90% in total onto the binder and it has a good dispersion and good macroscopic distribution through the catalyst grain which constitutes the preferred preparation method.

Optionally, at least one other metal selected from the group formed by elements from groups IB, IIB, IIIA, IVA, VIB and VIIB of the periodic table is also introduced. Any of the deposition techniques known to the skilled person and any precursor can be used to introduce at least one additional.

One preferred method for preparing the catalyst, prepared using the process of the invention, consists of milling the zeolite in a moist gel of matrix (generally obtained by mixing at least one acid and powdered matrix), for example alumina, for a period required to obtain good homogeneity of the paste produced, namely, for example, for about ten minutes, then passing the paste through a die to form extrudates, for example with a diameter in the range 0.4 to 4 mm, limits included. Then after oven drying, for example for several hours at about 120° C., and after calcining, for example for two hours at about 500° C. at least one element, for example platinum, is deposited, for example by anion exchange with hexachloroplatinic acid in the presence of a competing agent (for example hydrochloric acid), said deposition being followed by calcining, for example for about 2 hours at about 500° C.

Platinum is generally introduced into the matrix in the form of hexachloroplatinic acid, but ammoniacal compounds or compounds such as ammonium chloroplatinate, discarbonyl platinum dichloride, hexahydroxyplatinic acid, palladium chloride or palladium nitrate can be used for all noble metals.

In the present invention, at least one noble metal from the platinum family can, for example, be used by dint of ammoniacal compounds. In this case, the noble metal will be deposited onto the zeolite.

For platinum, examples which can be cited are platinum II tetramine salts with formula $Pt(NH_3)_4X_2$, platinum IV hexamine salts with formula $Pt(NH_3)_6X_4$; platinum IV halogenopentamine salts with formula $(PtX(NH_3)_5)X_3$; platinum N tetrahalogenodiamine salts with formula $PtX_4(NH_3)_2$; and complexes of platinum with halogen-polyketones and halogenated compounds with formula $H(Pt(acac)_2X)$; X being a halogen selected from the group formed by chlorine, fluorine, bromine and iodine, X preferably being chlorine, and acac representing the group $C_5H_7O_2$ derived from acetylacetone.

The noble metal from the platinum family is preferably introduced by impregnation using an aqueous or organic solution of one of the organometallic compounds cited above. Of the organic solvents which can be used, paraffinic, naphthenic or aromatic hydrocarbons can be cited, and halogenated organic compounds containing, for example, 1 to 12 carbon atoms per molecule. Examples which can be cited are n-heptane, methylcyclohexane, toluene and chloroform. Mixtures of solvents can also be used.

The additional metal, optionally introduced in addition, selected from the group formed by elements from groups IB, IIB, IIIA, IVA, VIB and VIIB, can be introduced via compounds such as chlorides, bromides and nitrates, alkyls of elements from groups IB, IIB, IIIA, IVA, VIB and VIIB, namely, for example, tin and indium, alkyl tin, indium nitrate and chloride.

This metal can also be introduced in the form of at least one organic compound selected from the group formed by complexes of said metal, in particular polyketone complexes of metal and hydrocarbylmetals such as metal alkyls, cycloalkyls, aryls, alkylaryls and arylalkyls. In the latter case, the metal is advantageously introduced using a solution of an organometallic compound of said metal in an organic solvent. Metal organohalogenated compounds can also be used. Particular metal compounds which can be cited are tetrabutyltin in the case of tin, triphenylindium in the case of indium.

The impregnating solvent is selected from the group formed by paraffinic, naphthenic and aromatic compounds containing 6 to 12 carbon atoms per molecule and halogenated organic compounds containing 1 to 12 carbon atoms per molecule. Examples are n-heptane, methylcyclohexane and chloroform. It is also possible to use mixtures of the solvents defined above.

It is also possible to introduce at least one metal selected from the group formed by elements from groups IB, IIB, IIIA, IVA, VIB and VIIB. This additional metal can optionally be introduced at any time during preparation, preferably prior to deposition of one of more of the group VIII metals. If this metal is introduced before the noble metal, the metal compound used is generally selected from the group formed by the metal halide, nitrate, acetate, tartrate, carbonate and oxalate. Introduction is the advantageously carried out in aqueous solution. However, it can also be introduced using a solution of an organometallic compound, for example tetrabutyltin. In this case, before introducing at least one noble metal, calcining in air is carried out.

The catalyst of the invention is generally formed so that the catalyst is preferably put into the form of extrudates or beads to suit its application.

Preparation of the catalyst is generally finished by calcining, normally at a temperature in the range from about 250° C. to 600° C., limits included, for a period of about 0.5 to 10 hours, preferably preceded by drying, for example oven drying, at a temperature in the range from ambient temperature to 250° C., preferably in the range 40° C. to 200° C. Said drying step is preferably carried out during the rise in temperature required to carry out said calcining step.

When the catalyst of the present invention contains sulphur, sulphur is introduced into the formed, calcined catalyst containing the metal or metals cited above, either in situ before the catalytic reaction, or ex-situ. Sulphurisation can optionally be carried out after reduction. With in situ sulphurisation, if the catalyst has not already been reduced, reduction is carried out before sulphurisation. With ex-situ sulphurisation, reduction is carried out followed by sulphurisation. Sulphurisation is carried out in the presence of hydrogen using any sulphurising agent which is known to the skilled person, such as dimethyl sulphide or hydrogen sulphide. As an example, the catalyst is treated with a feed containing dimethyl sulphide in the presence of hydrogen, with a concentration such that the sulphur/metal atomic ratio is 1.5. The catalyst is then kept at about 400° C. for about 3 hours in a stream of hydrogen before injecting the feed.

The EUO zeolite based catalyst prepared using the process of the present invention is used for isomerising an aromatic C8 cut comprising, for example, either solely a mixture of xylene(s), or solely ethylbenzene, or a mixture of xylene(s) and ethylbenzene. The process is generally carried out under the following operating conditions:

- a temperature in the range 300° C. to 500° C., preferably in the range 320° C. to 450° C., and more preferably in the range 340° C. to 430° C.;
- a partial hydrogen pressure in the range 0.3 to 1.5 MPa, preferably in the range 0.4 to 1.2 MPa, and more preferably 0.7 to 1.2 MPa;
- a total pressure in the range 0.45 to 1.9 MPa, preferably in the range 0.6 to 1.5 MPa;
- a space velocity, expressed as kilograms of feed introduced per kilogram of catalyst per hour, in the range 0.25 to 30 $h^{-1}$, preferably in the range 1 to 10 $h^{-1}$, and more preferably in the range 2 to 6 $h^{-1}$.

The invention will now be illustrated by the following examples.

EXAMPLES 1 TO 17

Synthesis of EU-1 (or TPZ-3) zeolite with an Si/Al ratio of 15 with hexamethonium bromide as the organic structuring agent and zeolite seeds with a different structure and/or Si/Al ratio, with an Si/Al ratio <200.

Examples 1 and 2 correspond to syntheses carried out without adding seeds, for comparison. Examples 3 to 17 correspond to syntheses carried out with zeolite seeds the characteristics of which are reported below.

The zeolites added as seeds were in different cationic forms (Na, K, $NH_4$, $NH_4$+TMA, Na+Hz, H) and in the form of particles with different sizes (3 to 115 μm for the mean diameter, DV,50). These seeds were different from the EU-1 solid synthesised as regards their structure type and/or Si/Al ratio.

The synthesis mixture had the following composition:

| | |
|---|---|
| $SiO_2$ (mol) | 60 |
| $Al_2O_3$ (mol) | 2 |
| $Na_2O$ (mol) | 10 |
| $HxBr_2$ (mol) | 20 |
| $H_2O$ (mol) | 2800 |
| Seeds/$SiO_2$ (g/g) | 0 (ex. 1 & 2), or 0.02 (ex. 3 to 16) |

$HxBr_2$ = hexamethonium bromide = $Me_3N(CH_2)_6NMe_3^{2+}(Br)_2$

| | | | | Seeds | | | |
|---|---|---|---|---|---|---|---|
| Examples | Zeolite | Structure type | Si/Al (mol/mol) | Form (cations) | Dv, 10 (μm) | Dv, 50 (μm) | Dv, 90 (μm) |
| 3 (invention) | ZSM-5 | MFI | 14.3 | Na | 48 | 115 | 205 |
| 4 (invention) | ZSM-5 | MFI | 27.7 | H | 52 | 107 | 173 |
| 5 (invention) | ZSM-5 | MFI | 76.5 | H | 2.8 | 5.8 | 24 |
| 6 (invention) | ZSM-5 | MFI | 150 | H | 1.7 | 4.8 | 14 |
| 7 (comparative) | silicalite | MFI | >500 | — | 1.4 | 2.7 | 5.2 |
| 8 (invention) | A | LTA | 1.0 | K | 1.1 | 5.3 | 11 |
| 9 (invention) | X | FAU | 1.3 | Na | 1.3 | 3.4 | 8.7 |
| 10 (invention) | Y | FAU | 2.8 | $NH_4$ | 1.4 | 3.1 | 7.0 |
| 11 (invention) | mordenite | MOR | 118 | H | 5.1 | 15 | 26 |
| 12 (invention) | mordenite | MOR | 5 | $NH_4$ | 5.1 | 15 | 26 |

-continued

| Examples | Zeolite | Structure type | Si/Al (mol/mol) | Seeds Form (cations) | Dv, 10 ($\mu$m) | Dv, 50 ($\mu$m) | Dv, 90 ($\mu$m) |
|---|---|---|---|---|---|---|---|
| 13 (invention) | mazzite | MAZ | 3.6 | $NH_4$ + TMA | 7.0 | 18 | 25 |
| 14 (invention) | EU-1 | EUO | 25.2 | $NH_4$ | 3.0 | 16 | 26 |
| 15 (invention) | EU-1 | EUO | 69.7 | Na + Hx | 3.0 | 16 | 40 |
| 16 (invention) | EU-1 | EUO | 144 | Na + Hx | 3.2 | 17 | 33 |
| 17 (comparative) | EU-1 | EUO | >500 | Na + Hx | 1.5 | 2.9 | 5.8 |

TMA = tetramethylammonium
Hx = hexamethonium
Dv, X = diameter of the equivalent sphere of particles where X % by volume of particles have a size less than that diameter.

A solution A composed of silica and structuring agent was prepared by diluting 12.03 g of hexamethonium bromide (Fluka, 97%) in 57.42 g of water then adding 14.50 g of colloidal silica sol (Ludox HS40, Dupont, 40% $SiO_2$). 0.985 g of solid sodium hydroxide (Prolabo, 99%) and 0.715 g of solid sodium aluminate (Prolabo, 46% $Al_2O_3$, 33% $Na_2O$) were then dissolved in 7.18 g of water to form a solution B. Solution B was added to solution A with stirring, then 7.18 g of water. Mixing was carried out until the medium was homogeneous and 0.116 g (Examples 3 to 17) of dried zeolite seeds were added (no seeds were added for Examples 1 and 2). The resulting mixture was reacted in a 125 ml autoclave with stirring at 180° C. under autogenous pressure. After cooling, the product was filtered and washed with 0.5 liters of demineralised water than dried in a ventilated oven at 120° C.

The results of X ray diffraction and chemical analysis are shown in Table 1, as a function of adding seeds or not and of the different zeolites added as seeds. The use of different zeolites with a Si/Al ratio of less than 200 as seeds (Examples 3 to 6 and 8 to 16) led to pure EU-1 zeolite (100±3% crystallinity, Si/Al ratio close to 15), with a maximum yield (about 5%) in 96 hours at 180° C. Under identical conditions, tests with zeolite seeds with an Si/Al ratio of more than 200 produced a solid which was not completely crystalline in EU-1 zeolite (Examples 7 to 17). Under identical conditions, the experiment with no seed addition (Example 2) produced no EU-1 zeolite. Thus in Example 1, synthesis had to be continued for 125 hours to allow pure EU-1 zeolite to be formed with a maximum yield.

EXAMPLES 18 TO 33

Synthesis of ZSM-50 zeolite with an Si/Al ratio of 125 with precursors of dibenzyldimethylammonium chloride as the organic structuring agent and zeolite seeds with a different structure and/or Si/Al ratio, with an Si/Al ratio <200.

Examples 18 and 19 correspond to syntheses carried out without adding seeds for comparison. Examples 20 to 33 correspond to syntheses carried out with zeolite seeds identical to those used in the preceding examples.

The synthesis mixture had the following composition:

| | |
|---|---|
| $SiO_2$ (mol) | 60 |
| $Al_2O_3$ (mol) | 0.24 |
| $Na_2O$ (mol) | 3.6 |
| BDMA (mol) | 6 |
| BCl (mol) | 6 |
| $H_2O$ (mol) | 1000 |
| Seeds/$SiO_2$ (g/g) | 0 (ex. 18 & 19), or 0.02 (ex. 20 to 33) |

BDMA = benzyldimethylamine
BCl = benzyl chloride

A solution C composed of silica and structuring agent precursors was prepared by diluting 3.537 g of benzyldimethylamine (Fluka, 98%) and 3.274 g of benzyl chloride (Fluka, 99%) in 42.72 g of water then adding 38.43 g of colloidal silica sol (Ludox HS40, Dupont, 40% $SiO_2$). 1.133 g of solid sodium hydroxide (Prolabo, 99%) and 0.227 g of solid sodium aluminate (Prolabo, 46% $Al_2O_3$, 33% $Na_2O$) were then dissolved in 5.34 g of water to form a solution D. Solution D was added to solution C with stirring, then 5.34 g of water. Mixing was carried out until the medium was homogeneous and 0.307 g (Examples 20 to 33) of dried zeolite seeds were added (no seeds were added for Examples 18 and 19). The resulting mixture was reacted in a 125 ml autoclave with stirring at 160° C. under autogenous pressure for 75–98 hours. After cooling, the product was filtered and washed with 1.5 liters of demineralised water then dried in a ventilated oven at 120° C.

The results of X ray diffraction and chemical analysis are shown in Table 2, as a function of adding seeds or not and of the different zeolites added as seeds. The use of different zeolites with a Si/Al ratio of less than 200 as seeds (Examples 20 to 23 and 25 to 32) led to pure EU-1, ZSM-50 zeolites (100±3% crystallinity, Si/Al ratio close to 125), with a maximum yield (about 15%) in 75 hours at 160° C.

Under identical conditions, tests with zeolite seeds with a high Si/Al ratio produced a solid which was not completely crystalline in EU-1 and ZSM-50 zeolite (Examples 24 and 33). Under identical conditions, the experiment with no seed addition (Examples 2 and 19) produced neither EU-1 zeolite nor ZSM-50 zeolite. Thus in Example 1 and Example 18, synthesis had to be continued for 125 hours or 98 hours to allow pure EU-1 zeolite and ZSM-50 zeolite to form with a maximum yield.

TABLE 1

Syntheses of EU-1 or TPZ-3 zeolites with Si/Al ratio close to 15 with zeolite seeds with a variety of structure types and Si/Al ratios

| Example no. | 1 (comparative) | 2 (comparative) | 3 | 4 | 5 | 6 | 7 (comparative) | 8 | 9 |
|---|---|---|---|---|---|---|---|---|---|
| Gel | | | | | | | | | |
| Formulation | 60 $SiO_2$ - 2 $Al_2O_3$ - 10 $Na_2O$ - 20 $HxBr_2$ - 2800 $H_2O$ - 2% seeds | | | | | | | | |
| Seeds | None | None | Na-ZSM-5 Si/Al = 14.3 | H-ZSM-5 Si/Al = 25.71 | H-ZSM-5 Si/Al = 76.5 | H-ZSM-5 Si/Al = 150 | Silicalite Si/Al >500 | K—A Si/Al = 1.0 | Na—X Si/Al = 1.3 |
| Crystallization | | | | | | | | | |
| Temperature (° C.) | | | | | 180 | | | | |
| Time (h) | 125 | | | | | 96 | | | |
| Solid | | | | | | | | | |
| Phase (XRD) | 100% EU-1 | AMO | 101% EU-1 | 98% EU-1 | 97% EU-1 | 99% EU-1 | 85% EU-1 + AMO | 102% EU-1 | 100% EU-1 |
| Si/Al (XF) | 15.4 | nd | 13.8 | 14.2 | 13.8 | 14.5 | nd | 13.7 | 14.9 |
| Solid yield (%) | 5.3 | 6.1 | 5.1 | 5.4 | 5.2 | 4.9 | 5.1 | 5.7 | 5.1 |

| Example no. | 10 | 11 | 12 | 13 | 14 | 15 | 16 | 17 (comparative) |
|---|---|---|---|---|---|---|---|---|
| Gel | | | | | | | | |
| Formulation | 60 $SiO_2$ - 2 $Al_2O_3$ - 10 $Na_2O$ - 20 $HxBr_2$ - 2800 $H_2O$ - 2% seeds | | | | | | | |
| Seeds | NH4-Y Si/Al = 2.8 | H-MOR Si/Al = 118 | NH4-MOR Si/Al = 5 | NH4-TMA-MAZ Si/Al = 3.6 | Na-Hx-EU-1 Si/Al = 25.2 | Na-Hx-Eu-1 Si/Al = 69.7 | Na-Hx-EU-1 Si/Al = 144 | Na-Hx-EU-1 Si/Al >500 |
| Crystallization | | | | | | | | |
| Temperature (° C.) | | | | 180 | | | | |
| Time (h) | | | | 96 | | | | |
| Solid | | | | | | | | |
| Phase (XRD) | 101% EU-1 | 99% EU-1 | 100% EU-1 | 99% EU-1 | 100% EU-1 | 102% EU-1 | 103% EU-1 | 90% EU-1 + AMO |
| Si/Al (XF) | 14.7 | 13.9 | 15.1 | 13.8 | 13.9 | 14.1 | 13.8 | nd |
| Solid yield (%) | 5.4 | 5.3 | 5.1 | 5.6 | 5.2 | 5.6 | 5.1 | 5.7 |

AMO = amorphous
Hx = hexamethonium
XF = X ray fluorescence
TMA = tetramethylammonium
XRD = X ray diffraction, with Example 1 as reference.

TABLE 2

Syntheses of ZSM-50 zeolites with Si/Al ratio close to 125 with zeolite seeds with a variety of structure types and Si/Al ratios

| Example no. | 18 (comparative) | 19 (comparative) | 20 | 21 | 22 | 23 | 24 (comparative) | 25 |
|---|---|---|---|---|---|---|---|---|
| Gel | | | | | | | | |
| Formulation | 60 $SiO_2$ - 0.3 $Al_2O_3$ - 10 $Na_2O$ - 20 $HxBr_2$ - 2800 $H_2O$ - 2% seeds | | | | | | | |
| Seeds | None | None | Na-ZSM-5 Si/Al = 14.3 | H-ZSM-5 Si/Al = 25.7 | H-ZSM-5 Si/Al = 76.5 | H-ZSM-5 Si/Al = 150 | Silicate Si/Al >500 | K—A Si/Al = 1.0 |

TABLE 2-continued

Syntheses of ZSM-50 zeolites with Si/Al ratio close to 125 with zeolite seeds with a variety of structure types and Si/Al ratios

| | | | | Crystallization | | | | |
|---|---|---|---|---|---|---|---|---|
| Temperature (° C.) | | | | | 160 | | | |
| Time (h) | 98 | | | | 75 | | | |
| | | | | Solid | | | | |
| Phase (XRD) | 100% ZSM-50 | AMO | 97% ZSM-50 | 99% ZSM-50 | 99% ZSM-50 | 100% ZSM-50 | 75% ZSM-50 + AMO | 101% ZSM-50 |
| Si/Al (XF) | 133 | nd | 139 | 122 | 1?8 | 135 | nd | 109 |
| Solid yield (%) | 15.5 | 17.1 | 15.2 | 16.0 | 15.3 | 15.8 | 15.6 | 15.5 |
| Example no. | 26 | 27 | 28 | 29 | 30 | 31 | 32 | 33 |
| | | | | Gel | | | | |
| Formulation | 60 $SiO_2$ - 0.3 $Al_2O_3$ - 10 $Na_2O$ - 20 $HxBr_2$ - 2800 $H_2O$ - 2% seeds | | | | | | | |
| Seeds | Na—X Si/Al = 1.3 | NH4-Y Si/Al = 2.8 | NH4-MOR Si/Al = 118 | NH4-TMa-MAZ Si/Al = 3.6 | Na-Hx-Eu-1 Si/Al = 25.2 | Na-Hx-EU-1 Si/Al = 69.7 | Na-Hx-EU-1 Si/Al = 144 | Na-Hx EU-1 Si/Al >500 |
| | | | | Crystallization | | | | |
| Temperature (° C.) | | | | | 160 | | | |
| Time (h) | | | | | 75 | | | |
| | | | | Solid | | | | |
| Phase (XRD) | 103% ZSM-50 | 98% ZSM-50 | 101% ZSM-50 | 98% ZSM-50 | 100% ZSM-50 | 102% ZSM-50 | 98% ZSM-50 | 85% ZSM-50 + AMO |
| Si/Al (XF) | 113 | 123 | 132 | 121 | 131 | 146 | 137 | nd |
| Solid yield (%) | 15.2 | 15.0 | 15.8 | 18.9 | 15.6 | 15.0 | 14.8 | 16.2 |

AMO = amorphous
BDMA = benzylidimethylamine
XRD = X ray diffraction, with Example 17 as reference
TMA = tetramethylammonium
BCl = benzyl chloride
XF = X ray fluorescence
Hx = hexamethonium

EXAMPLE 34

Preparation of a Catalyst A, Not in Accordance with the Invention, Containing EU-1 Zeolite Synthesised in the Absence of Seeds as Described in Example 1 and 0.3% by Weight of Platinum The starting material used was as an synthesised EU-1 zeolite comprising the organic structuring agent, silicon and aluminium, with an overall Si/Al atomic ratio of 15.4 and a sodium content of about 1.5% with respect to the weight of dry EU-1 zeolite.

This EU-1 zeolite first underwent dry calcining at 550° C. in a stream of air for 6 hours. The solid obtained underwent three ion exchange steps in a 10 N $NH_4HO_3$ solution at about 100° C. for 4 hours for each exchange.

At the end of these treatments, the EU-1 zeolite in its $NH_4$ form had an overall Si/Al atomic ratio of 19.9 and a sodium content of 55 ppm by weight with respect to the weight of dry EU-1 zeolite.

The EU-1 zeolite was then formed by extrusion with an alumina gel to obtain, after drying and calcining in dry air, a support S1 constituted by 1.4 mm diameter extrudates containing 10% by weight of EU-1 zeolite in the H form and 90% of alumina.

The support S1 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst A produced contained, by weight, 10.0% of EU-1 zeolite in its hydrogen form, 89.7% of alumina and 0.3% of platinum.

EXAMPLE 35

Preparation of a Catalyst B, in Accordance with the Invention, Containing EU-1 Zeolite Synthesised in the Presence of $NH_4$—Y Seeds as Described in Example 10 and 0.3% by Weight of Platinum The starting material used was as synthesised EU-1 zeolite comprising the organic structuring agent, silicon and aluminium, with an overall Si/Al atomic ratio of 14.7 and a sodium content of about 1.4% with respect to the weight of dry EU-1 zeolite. p This EU-1 zeolite first underwent dry calcining at 550° C. in a stream of air for 6 hours. The solid obtained underwent three ion exchange steps in a 10 N $NH_4NO_3$ solution at about 100° C. for 4 hours for each exchange.

At the end of these treatments, the EU-1 zeolite in its NH$_4$ form had an overall Si/Al atomic ratio of 19.2 and a sodium content of 30 ppm by weight with respect to the weight of dry EU-1 zeolite.

The EU-1 zeolite was then formed by extrusion with an alumina gel to obtain, after drying and calcining in dry air, a support S2 constituted by 1.4 mm diameter extrudates containing 10% by weight of EU-1 zeolite in the H form and 90% of alumina.

The support S2 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst B produced contained, by weight, 10.0% of EU-1 zeolite in its hydrogen form, 89.7% of alumina and 0.3% of platinum.

EXAMPLE 36

Preparation of a Catalyst, C, in Accordance with the Invention, Containing EU-1 Zeolite Synthesised in the Presence of MOR Seeds (Si/Al=5) as Described in Example 12 and 0.3% by Weight of Platinum The starting material used was as synthesised EU-1 zeolite comprising the organic structuring agent, silicon and aluminium, with an overall Si/Al atomic ratio of 13.9 and a sodium content of about 1.5% with respect to the weight of EU-1 zeolite.

This EU-1 zeolite first underwent dry calcining at 550° C. in a stream of air for 6 hours. The solid obtained underwent three ion exchange steps in a 10 N NH$_4$NO$_3$ solution at about 100° C. for 4 hours for each exchange.

At the end of these treatments, the EU-1 zeolite in its NH$_4$ form had an overall Si/Al atomic ratio of 18.5 and a sodium content of 45 ppm by weight with respect to the weight of dry EU-1 zeolite.

The EU-1 zeolite was then formed by extrusion with an alumina gel to obtain, after drying and calcining in dry air, a support S3 constituted by 1.4 mm diameter extrudates containing 10% by weight of EU-1 zeolite in the H form and 90% of alumina.

The support S3 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst C produced contained, by weight, 10.0% of EU-1 zeolite in its hydrogen form, 89.7% of alumina and 0.3% of platinum.

EXAMPLE 37

Preparation of a Catalyst, C, in Accordance with the Invention, Containing EU-1 Zeolite Synthesised in the Presence of Silicate Seeds (Si/Al>500) as Described in Example 7 and 0.3% by Weight of Platinum The starting material used was incompletely crystallised (85% EU-1+amorphous) as synthesised EU-1 zeolite with an overall Si/Al atomic ratio which could not be determined. The sodium content was about 1.5% with respect to the weight of EU-1 zeolite.

This EU-1 zeolite first underwent dry calcining at 550° C. in a stream of air for 6 hours. The solid obtained underwent three ion exchange steps in a 10 N NH$_4$NO$_3$ solution at about 100° C. for 4 hours for each exchange.

At the end of these treatments, the EU-1 zeolite in its NH$_4$ form had an overall Si/Al atomic ratio of 18.5 and a sodium content of 40 ppm by weight with respect to the weight of dry EU-1 zeolite.

The EU-1 zeolite was then formed by extrusion with an alumina gel to obtain, after drying and calcining in dry air, a support S4 constituted by 1.4 mm diameter extrudates containing 10% by weight of EU-1 zeolite in the H form and 90% of alumina.

The support S4 obtained underwent anionic exchange with hexachloroplatinic acid in the presence of a competing agent (hydrochloric acid), so as to deposit 0.3% by weight of platinum with respect to the catalyst. The moist solid was dried at 120° C. for 12 hours and calcined in a stream of dry air at a temperature of 500° C. for one hour.

Catalyst D produced contained, by weight, 10.0% of EU-1 zeolite in its hydrogen form, 89.7% of alumina and 0.3% of platinum.

EXAMPLE 38

Evaluation of Catalytic Properties of Catalysts A, B, C and D by Isomerising an Aromatic C8 Cut The performances of catalysts A, B, C and D were evaluated by isomerising an aromatic C8 cut principally containing meta-xylene, ortho-xylene and ethylbenzene. The operating conditions were as follows:

temperature: 390° C.
total pressure: 15 bar, (1 bar=0.1 MPa);
hydrogen partial pressure: 12 bar.

The catalysts were laboratory tested, using 5 g and with no hydrogen recycle.

The catalysts were first treated with a feed containing dimethyl disulphide (DMDS) in the presence of hydrogen, with a concentration such that the sulphur/metal atomic ratio was 1.5. The catalyst was then maintained for 3 hours at 400° C. in a stream of hydrogen then the feed was injected.

The catalysts were compared in terms of their activity (by approximate equilibria of para-xylene and ethylbenzene, and by ethylbenzene conversion) and their selectivity by net losses at iso-approximate equilibrium of para-xylene.

Side reactions lead to three types of losses: losses to paraffins essentially resulting from naphthene ring opening reactions followed by cracking; losses to aromatics formed by dismutation and transalkylation of aromatic compounds containing 8 carbon atoms (AC8) and finally, losses to naphthalenes, namely naphthenes containing 8 carbon atoms (N8) due to hydrogenation of aromatic compounds. N8 can be recycled, so the losses by cracking and dismutation/transalkylation including naphthenes other than N8 are compared (the sum of which constitutes net losses).

In order to calculate the approximate equilibrium (AEQ), the concentrations of para-xylenes (%pX) are expressed with respect to the three xylene isomers.

The approximate equilibrium (AEQ) is defined as follows:

$$pXAEQ(\%)=100\times(\%pX_{effluent}-\%pX_{feed})/(\%pX_{equilibrium}-\%pX_{feed})$$

The cracking losses (P1) are the AC8 losses in the form of C1 to C8 paraffins (PAR):

$$P1(wt\%)=100\times[(\%PAR_{effluent}\times weight\ of\ effluent)-(\%PAR_{feed}\times weight\ of\ feed)]/(\%AC8_{feed}\times weight\ of\ feed)$$

The dismutation/transalkylation losses (P2) are the AC8 losses in the form of naphthenes other than N8, toluene, benzene and C9+aromatics (OAN):

$$P2(wt\%)=100\times[(\%OAN_{effluent}\times weight\ of\ effluent)-(\%OAN_{feed}\times weight\ of\ feed)]/(\%AC8_{feed}\times weight\ of\ feed)$$

The sum of losses P1 and P2 represents the net losses.

The data shown in Table 3 were obtained under iso-experimental conditions.

TABLE 3

| Catalysts | A (comp) | B (inv) | C (inv) | D (comp) |
|---|---|---|---|---|
| pX AEQ (%) | 97.8 | 98.0 | 98.2 | 85.2 |
| EB conversion (%) | 59.5 | 59.3 | 59.8 | 36.2 |

It can be seen from the results shown in Table 3 that catalysts B and C of the invention lead to results which were comparable with those obtained with catalyst A which was not in accordance with the invention, and that catalyst D which was not in accordance was much less active than the three other catalysts.

These catalysts were also compared at a lower pX AEQ (about 95.5%) by varying the mass flow rate of the feed. These results are shown in Table 4.

TABLE 4

| Catalysts | A (comp) | B (inv) | C (inv) | D (comp) |
|---|---|---|---|---|
| pX AEQ (%) | 95.3 | 95.5 | 95.1 | 95.1 |
| Net losses (wt %) | 4.9 | 5.1 | 4.7 | 4.8 |

At an iso pX AEQ of about 95.5%, Table 4 shows that the catalysts are all selective as well.

The activity and selectivity obtained during use of catalysts B and C, based on zeolites with structure type EUO, obtained using $NH_4$—Y and MOR seeds respectively, for isomerisation of an aromatic C8 cut are thus comparable with those of a catalyst containing a zeolite with structure type EUO with a similar Si/Al ratio and obtained using a synthesis mode which does not involve seeds described in the prior art. Catalyst D obtained using seeds not in accordance with the invention (Si/Al>500) was substantially less active than the others.

Finally, catalysts A, B, C and D were compared as regards stability over time under the experimental conditions described at the beginning of the example and over a duration of 400 hours.

Stability was evaluated from the evolution of ethylbenzene conversion. The results are shown in Table 5.

TABLE 5

| Catalysts | A (comp) | B (inv) | C (inv) | D (comp) |
|---|---|---|---|---|
| EB conversion (%) at t = 36 h | 59.5 | 59.3 | 59.8 | 36.2 |
| EB conversion (%) at t = 400 h | 54.4 | 53.9 | 53.8 | 35.1 |
| Drop in EB conversion (%) | 3.2 | 3.4 | 3.1 | 3.1 |

It can be seen that the deactivation of the four catalysts A, B, C and D over 400 hours was comparable.

The catalytic properties (activity, selectivity and stability) of the three catalysts, A, B and C are comparable. Introducing this novel mode of synthesising zeolite with structure type EUO in the preparation of this catalyst for isomerising aromatic C8 cuts is thus a substantial advantage as regards cost since the zeolite synthesis time is reduced by about 25% while the catalytic properties of the catalyst of the invention are preserved. The use of zeolite seeds with a Si/Al ratio of <200 is indispensable for producing a zeolite with structure type EUO leading to a good catalyst. In fact, the activity of catalyst D was substantially lower.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French applications 98/13.839 and 98/16.412, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a zeolitic material with structure type EUO comprising an element X selected from silicon and germanium and at least one element T selected from iron, aluminium, gallium, boron, titanium, vanadium, zirconium, molybdenum, arsenic, antimony, chromium and manganese, characterized in that seeds of at least one zeolitic material comprising at least one element X' selected from silica and germanium and at least one element T' selected from iron, aluminium, gallium, boron, titanium, vanadium, zirconium, molybdenum, arsenic, antimony, chromium and manganese is used with an X'/T' ratio of less than 200, said seeds being different from the zeolite with structure type EUO which is prepared.

2. A process according to claim 1, in which the structure type of the zeolitic material seeds is different from the EUO structure type.

3. A process according to claim 1, in which the chemical composition of the crystalline framework of the seeds is different from the chemical composition of the crystalline framework of the zeolite with structure type EUO which is prepared.

4. A process according to claim 1, in which the zeolitic material used as seeds is selected from zeolites with structure type LTA, structure type LTL, structure type FAU, structure type MOR, structure type MAZ, structure type OFF, structure type FER, structure type ERI, structure type BEA, structure type MFI, structure type MTW, structure type MTT, structure type LEV, structure type TON, structure type NES, or a NU-85, NU-86, NU-88 or IM-5 zeolite or a zeolite with structure type EUO with a chemical composition of the crystalline framework which is different from the EUO zeolite which is prepared.

5. A process according to claim 4, in which the seeds used are selected from seeds of at least one zeolitic material with structure type LTA, FAU, MOR, MFI or EUO.

6. A process according to claim 1, comprising synthesising an aqueous mixture comprising at least one source of at least one element X and at least one source of at least one element T, at least one source of an organic structuring agent and seeds of at least one zeolitic material.

7. A process according to claim 6, in which the zeolitic material seeds are introduced at any point in the preparation.

8. A process according to claim 6, in which the zeolitic material seeds are introduced after at least partial homogenisation of the aqueous mixture containing the source of element X, the source of element T and the source of the organic structuring agent.

9. A process according to claim 1, in which the element X is silicon and the element T is aluminium.

10. A process according to claim 6, in which the organic structuring agent is an alkylated polymethylene α-ω diammonium derivative with formula: $R_1R_2R_3N^+(CH_2)_nN^+R_4R_5R_6$ and/or an amine degradation product corresponding to said derivative and/or a precursor corresponding to said derivative, n being in the range 3 to 12 and $R_1$ to $R_6$, which may be identical or different, optionally representing alkyl or hydroxyalkyl radicals containing 1 to 8 carbon atoms, and up to five radicals $R_1$ to $R_6$ optionally being hydrogen.

11. A process according to claim 6, in which the organic structuring agent is a compound comprising dibenzyldimethylammonium and/or an amine degradation product corresponding to said derivative and/or a precursor corresponding to said derivative.

12. A process according to claim 6, in which at least one alkali metal or ammonium salt is introduced.

13. A process according to claim 6, in which the reaction mixture has the following composition, expressed in the oxide form:

| | |
|---|---|
| $XO_2/T_2O_3$ (mol/mol) | at least 10 |
| $OH^-/XO_2$ (mol/mol) | 0.002 to 2.0 |
| $Q/XO_2$ (mol/mol) | 0.002 to 2.0 |
| $Q/(M^+ + Q)$ (mol/mol) | 0.1 to 1.0 |
| $H_2O/XO_2$ (mol/mol) | 1 to 500 |
| $P/XO_2$ (mol/mol) | 0 to 5 |
| $S/XO_2$ (g/g) | 0.0001 to 0.1 | where

X is silicon and/or germanium,

T is at least one element selected from aluminium, iron, gallium, boron, titanium, vanadium, zirconium, molybdenum, arsenic, antimony, chromium and manganese;

$M^+$ represents an alkali metal or an ammonium ion;

Q represents the organic structuring agent or decomposition products corresponding to said derivative or precursors of said derivative;

S represents zeolite seeds expressed in their dried as synthesised, calcined or exchanged form with an X'/T' ratio of less than 200;

P represents an alkali metal or ammonium salt.

* * * * *

UNITED STATES PATENT AND TRADEMARK OFFICE
CERTIFICATE OF CORRECTION

PATENT NO. : 6,342,200 B1
DATED : January 29, 2002
INVENTOR(S) : Rouleau et al.

It is certified that error appears in the above-identified patent and that said Letters Patent is hereby corrected as shown below:

<u>Title page,</u>
Item [57], ABSTRACT,
Line 19, delete "isomerizing" and insert -- isomerising --.

Signed and Sealed this

Fifteenth Day of October, 2002

*Attest:*

JAMES E. ROGAN
*Attesting Officer*     *Director of the United States Patent and Trademark Office*